US006315996B1

(12) United States Patent
O'Callaghan

(10) Patent No.: US 6,315,996 B1
(45) Date of Patent: Nov. 13, 2001

(54) TOPICAL LYSOSTAPHIN THERAPY FOR STAPHYLOCOCCUS OCULAR INFECTIONS

(75) Inventor: Richard J. O'Callaghan, Slidell, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/289,684

(22) Filed: Apr. 9, 1999

(51) Int. Cl.[7] .............................. A61K 38/48; C12N 9/48; C12N 9/50
(52) U.S. Cl. ...................... 424/94.63; 435/212; 435/219
(58) Field of Search ................................... 435/212, 219; 424/94.63

(56) References Cited

U.S. PATENT DOCUMENTS

| 3,278,378 | 10/1966 | Schindler et al. | 424/115 |
|---|---|---|---|
| 3,398,056 | 8/1968 | Zygmunt et al. | 435/71.3 |
| 3,594,284 | 7/1971 | Zygmust et al. | 435/220 |
| 4,980,163 | 12/1990 | Blackburn et al. | 424/94.63 |
| 5,627,195 | * 5/1997 | Hu | 514/321 |

OTHER PUBLICATIONS

O'Callaghan, R., "Role of Exoproteins in Bacterial Keratitis: The Fourth Annual Thygeson Lecture, Presented at the Ocular Microbiology and Immunology Group Meeting, Nov. 7, 1998," Cornea, vol. 18, No. 5, pp. 532–537 (1999).
Evans, N., Ophthalmology, Oxford Univ. Press Inc., New York, p. 37, 1995.*
M.C. Callegan et al., "Pharmokinetic Considerations in the Treatment of Bacterial Keratitis," Clin. Pharmocokinet., vol. 27, pp. 129–149 (1994).
Physician's Desk Reference,50th Edition, Medical Economics Company, Montvale, New Jersey, pp. 472–474, 1456, 1481–1483, 1567, 1617, 2360–2361 (1996).
Smith et al., Emergence of vancomycin–resistant Staphylococcus aureus, New England Journal of Medicine, vol. 340, pp. 493–501 (1999).
C.A. Schindler et al., "Lysostaphin: A New Bacteriolytic Agent for the Staphylococcus," Proc.N.A.S., vol. 51, pp. 414–421 (1964).
Hiramatsu et al., "Methicillin–resistant Staphylococcus aureus clinical strain with reduced vancomycin susceptibility," Journal of Antimicrobial Chemotherapy, vol. 40, pp. 135–136 (1997).
C.A. Schindler et al., "Purification and Properties of Lysostaphin—A Lytic Agent for Staphylococcus aureus," Biochim. Biophys. Acta, vol. 97, pp. 242–250 (1965).
W.A. Zygmunt et al., "In Vitro Effect of Lysostaphin, Neomycin, and Bacitracin on Staphylococcus aureus," Canadian Journal of Microbiology, vol. 12, pp. 204–206 (1966).

W.A. Zygmunt et al., "Lytic action of Lysostaphin on Susceptible and Resistant Strains of Staphylococcus aureus," Canadian Journal of Microbiology, vol. 13, pp. 845–853 (1967).
W.A. Zygmunt et al., "Susceptibility of Coagulase–negative Staphylococcus to Lysostaphin and Other Antibiotics," Applied Microbiology, vol. 16, pp. 1168–1173 (1968).
W.A. Zygmunt et al., "Lysostaphin: Model for a Specific Enzymatic Approach to Infectious Disease," Progress in Drug Research, vol. 16, pp. 309–333 (1972).
H.P. Browder et al., "Lysostaphin: Enzymatic mode of action," Biochemical and Biophysical Research Communications, vol. 19, pp. 383–389 (1965).
A.J. Bramley et al., "Effects of lysostaphin on Staphylococcus aureus infections of the mouse mammary gland," Research in Veterinary Science, vol. 49, pp. 120–121 (1990).
E.R. Oldham et al., "Lysostaphin: Use of a Recombinant Bactericidal Enzyme as a Mastitis Therapeutic," J. Dairy Sci., vol. 74, pp. 4175–4182 (1991).
M.W. Climo et al., "Lysostaphin Treatment of Experimental Methicillin–Resistant Staphylococcus aureus Aortic Valve Endocarditis," Antimicrobial Agents and Chemotherapy, vol. 42, pp. 1355–1360 (1998).
R.R. Martin et al., "The selective activity of lysostaphin in vivo," Journal of Laboratory and Clinical Medicine, vol. 70, pp. 1–8 (1967).
K.E.Quickel, Jr., et al., "Efficacy and Safety of Topical Lysostaphin Treatment of Persistent Nasal Carriage of Staphylococcus aureus," Applied Microbiology, vol. 22, pp. 446–450 (1971).

(List continued on next page.)

*Primary Examiner*—Ponnathapu Achutamurthy
*Assistant Examiner*—Peter P. Tung
(74) *Attorney, Agent, or Firm*—Bonnie J. Davis; John H. Runnels

(57) ABSTRACT

A method has been discovered for using lysostaphin as an effective antibiotic for topical treatment of Staphylococcus corneal infections (keratitis). Lysostaphin applied topically to the cornea by eye drops killed bacteria within the cornea; lysostaphin reduced the number of bacteria from approximately 10,000,000 viable bacteria colony forming units ("CFU") in the untreated eye to essentially no viable bacteria in the treated eyes. Treatment by lysostaphin was more potent than any of the smaller antibiotics that have been previously tested (e.g., tetracyclines, erythromycins, cephalosporins, vancomycin, aminoglycosides, or fluoroquinolones). Moreover, topical application of lysostaphin was effective against the highly antibiotic-resistant Staphylococcus strains.

14 Claims, No Drawings

OTHER PUBLICATIONS

R. Aly et al., "Role of Teichoic Acid in the Binding of Staphylococcus aureus to Nasal Epithelial Cells," Journal of Infectious Diseases, vol. 141, pp. 463–465 (1980).

P.A. Recsei et al., "Cloning, sequence, and expression of the lysostaphin gene from Staphylococcus simulans," Proc. Natl. Acad. Sci. USA, vol. 84, pp. 1127–1131 (1987).

Park et al., "Binding and Degradation of Elastin by the Staphylolytic Enzyme Lysostaphin," Int. J. Biochem. Cell Biol., vol. 27, pp. 139–146 (1995).

Abstract by J.J. Dajcs et al., "Lysostaphin is effective in treating methicillin–resistant and methicillin–sensitive Staphylococcus aureus keratitis," IOVS, vol. 40, p. S262 (1999) to be presented at the 1999 meeting for the Association for Research in Vision and Ophthalmology, Fort Lauderdale, Florida, May 10, 1999.

* cited by examiner

TOPICAL LYSOSTAPHIN THERAPY FOR STAPHYLOCOCCUS OCULAR INFECTIONS

This invention pertains to a method to treat Staphylococcus infections of the eye.

The eye is relatively impermeable to micro-organisms and other environmental elements. However, if the integrity of the cornea is breached by trauma, a sight-threatening bacterial infection can result. *Staphylococcus aureus, Pseudomonas aeruginosa,* and *Streptococcus pneunoniae* are the most common bacterial pathogens associated with infection of compromised corneas. Bacterial enzymes and toxins, as well as factors associated with the host immune response, can lead to tissue destruction during corneal infection. A successful antibacterial agent must both be active against the pathogen and be able to reach the pathogen. See M. C. Callegan et al., "Pharmokinetic considerations in the treatment of bacterial keratitis," Clin. Pharmocokinet., vol. 27, pp. 129–149 (1994).

The cornea provides a protective barrier against invading organisms and other harmful substances. The cornea has three primary layers (epithelium, stroma, and endothelium) that maintain mechanical integrity, proper hydration, and transparency for adequate vision. Because the cornea is not vascularized, systemic drugs do not readily permeate the cornea and are generally not used for therapy of ocular bacterial infections. Topical application of antibiotics is the preferred delivery method. However, corneal impermeability presents a barrier not only to invading micro-organisms, but also to the penetration of many drugs into the eye, especially water-soluble antibacterial agents. For example, cephalosporins, aminoglycosides and penicillins diffuse less readily across the epithelium than lipid-soluble antibacterials, such as chlorampenicol and rifampicin. To facilitate diffusion across the cornea, antibiotics used to treat bacterial ocular infections are generally small molecules, with molecular weights between 300 and 1500 Daltons: cefazolin, 476 Daltons; ciprofloxacin, 356 Daltons; gentamicin, 463 Daltons; norfloxacin, 319 Daltons; ofloxacin, 361 Daltons; tobaymycin, 467 Daltons; and vancomycin, 1480 Daltons. See Callegan et al, 1994; and Physicians Desk Reference, 50$^{th}$ Edition, Medical Economics Company, Montvale, N.J., pp. 472–474, 1456, 1481–1483, 1567, 1617, 2360–2361 (1996).

Drug penetration into infected corneal tissues is a limitation of standard therapies that contributes to treatment failure.

Staphylococcus is the most frequently isolated bacterial genus involved in serious eye infections. *S. aureus* is found as flora of the face and anterior nostrils in asymptomatic carriers. This pathogen is readily transferred manually to an injured or compromised cornea. Without effective inhibition or killing of the infecting Staphylococcus, the eye can be damaged to such a degree that removal of the entire eye is necessary.

Staphylococcus is a genus of Gram-positive bacteria that has been recognized for decades as both a powerful pathogenic organism and a bacterium that frequently evolves new stages of antibiotic resistance. The development of new antimicrobial therapies for Staphylococcus infections is considered a high priority. Numerous antibiotics that were once effective against this organism are now unable to treat infections caused by many Staphylococcus strains. Among the most difficult strains to treat are those designated as methicillin-resistant *Staphylococcus aureus* ("MRSA"). MRSA strains are commonly isolated from hospital-acquired infections. Most MRSA strain can now be treated with only one commercially available antibiotic, vancomycin. Unfortunately, vancomycin is a slow-acting drug that often causes toxic reactions. Complicating the situation even further is the recent isolation of MRSA strains that do not respond to vancomycin therapy. See Smith et al., "Emergence of vancomycin-resistant *Staphylococcus aureus,* New England Journal of Medicine, vol. 340, pp. 493–501 (1999); and Hiramatsu et al., "Methicillin-resistant *Staphylococcus aureus* clinical strain with reduced vancomycin susceptibility," Journal of Antimicrobial Chemotherapy, vol. 40, pp. 135–136 (1997). Thus, there is a clear need for new drugs to treat Staphylococcus infections.

Keratitis caused by Staphylococcus is most often treated by chemotherapy. Topical cefazolin (5.0% in artificial tears), often used in combination with a fortified aminoglycoside (0.3%), and fluoroquinolones (0.3% ciprofloxacin or ofloxacin) are the antibiotics most often employed for treating Staphylococcus keratitis. (Callegan et al., 1994). Topical antibiotic drops are applied as frequently as once every 15 to 30 minutes for 48 hours or longer. Methicillin-resistant *Staphylococcus aureus* ("MRSA") strains resistant to multiple antibiotics have been treated successfully with ciprofloxacin; however, the susceptibility of MRSA strains to fluoroquinolones has declined rapidly in the past several years. Less than half of the recently-isolated MRSA strains remain susceptible. The increasing incidence of fluoroquinolone-resistant MRSA strains has dictated that vancomycin therapy (5.0%) be employed for most MRSA infections. Of greater importance is the recent emergence of MRSA stains not susceptible to vancomycin. The emergence of such strains has created a situation in which infected patients cannot be treated by any commercial antibiotic currently available; such strains have required use of experimental antibiotics for therapy.

Lysostaphin, a protein of 27,000 Daltons, is a bacterial endopeptidase that is highly lethal to *S. aureus* and *S. epidermidis.* It was initially isolated from a strain of *Staphylococcus simulans.* See C. A. Schindler et al., "Lysostaphin: A new bacteriolytic agent for the staphylococcus," Proc.N.A.S., vol. 51, pp. 414–421 (1964); C. A. Schindler et al., "Purification and properties of lysostaphin-a lytic agent for *Staphylococcus aureus,*" Biochim. Biophys. Acta, vol. 97, pp. 242–250 (1996); W. A. Zygmunt et al., "In vitro effect of lysostaphin, neomycin, and bacitracin on *Staphylococcus aureus,*" Canadian Journal of Microbiology, vol. 12, pp. 204–206 (1966); W.A. Zygmunt et al., "Lytic action of lysostaphin on susceptible and resistant strains of *Staphylococcus aureus,*" Canadian Journal of Microbiology, vol. 13, pp. 845–853 (1967); W. A. Zygmunt et al., "Susceptibility of coagulase-negative Staphylococcus to lysostaphin and other antibiotics," Applied Microbiology, vol. 16, pp. 1168–1173 (1968); W. A. Zygmunt et al., "Lysostaphin: Model for a specific enzymatic approach to infectious disease," Progress in Drug Research, vol. 16, pp. 309–333 (1972); and H. P. Browder et al., "Lysostaphin: Enzymatic mode of action," Biochemical and Biophysical Research Communications, vol. 19, pp. 383–389 (1965).

Lysostaphin has been shown to be effective in lowering *S. aureus* infections located internally (e.g., mastitis in mammary glands and aortic valve endocarditis) when lysostaphin was injected systemically or into the infected tissues. See A. J. Bramley et al., "Effects of lysostaphin on *Staphylococcus aureus* infections of the mouse mammary gland," Research in Veterinary Science, vol. 49, pp. 120–121 (1990); E. R. Oldham et al., "Lysostaphin: Use of a recombinant bactericidal enzyme as a mastitis therapeutic," J. Dairy Sci., vol. 74, pp. 4175–4182 (1991); and M. W. Climo et al., "Lysostaphin treatment of experimental methicillin-resistant *Staphylococcus aureus* aortic valve endocarditis," Antimicrobial Agents and Chemotherapy, vol. 42, pp. 1355–1360 (1998). Topical application of lysostaphin has been used to treat *S. aureus* attached to nasal epithelial cells in the nares. See R. R. Martin et al., "The selective activity of lysostaphin in vivo," Journal of Laboratory and Clinical Medicine, vol. 70, pp. 1–8 (1967); K. E. Quickel, Jr., et al., "Efficacy and safety of topical lysostaphin treatment of persistent nasal carriage of *Staphylococcus aureus*," Applied Microbiology, vol. 22, pp. 446–450 (1971); and R. Aly et al., "Role of teichoic acid in the binding of *Staphylococcus aureus* to nasal epithelial cells," Journal of Infectious Diseases, vol. 141, pp. 463–465 (1980). However, it has not been suggested that lysostaphin be applied topically to cross membranes to reach bacteria located inside the body.

Lysostaphin has also been found to be effective against MRSA strains by in vitro culture. It was more effective than the current antibiotic of choice, vancomycin, for infections due to MRSA strains. See M. W. Climo et al., 1998.

The lysostaphin gene has been sequenced and cloned. See P. A. Recsei et al., "Cloning, sequence, and expression of the lysostaphin gene from *Staphylococcus simulans*," Proc. Natl. Acad. Sci. USA, vol. 84, pp. 1127–1131 (1987).

U.S. Pat. No. 3,278,378 describes a process of producing a lytic antibiotic substance by culturing a strain of *Staphylococcus staphylolyticus*.

U.S. Pat. No. 3,398,056 describes a process of producing lysostaphin by fermentation.

U.S. Pat. No. 3,594,284 describes a process of producing lysostaphin by a reduced fermentation period using a cyclic process.

U.S. Pat. No. 4,980,163 describes a broad range bacteriocin composition, comprising lysostaphin and a lanthionine-containing bacteriocin.

I have discovered that lysostaphin, despite its large size, is an effective antibiotic for topical treatment of Staphylococcus corneal infections (keratitis). Lysostaphin can be used in an eye drop medication effective for treating common forms of Staphylococcus eye infections, including some of the most antibiotic-resistant forms. Lysostaphin therapy resulted in rapid bacterial killing without any irritation or toxicity associated with its ocular use. The penetration of lysostaphin into live corneal tissue was surprising because lysostaphin is much larger than antibiotics commonly used to treat corneal infections. Lysostaphin applied topically to the cornea by drops killed bacteria within the cornea; lysostaphin reduced the number of bacteria from approximately 10,000,000 viable bacteria colony forming units ("CFU") in the untreated eye to essentially no viable bacteria in the treated eyes. Treatment by lysostaphin was more potent than any of the smaller antibiotics that have been previously tested (e.g., tetracyclines, erythromycins, cephalosporins, vancomycin, aminoglycosides, or fluoroquinolones). Moreover, topical application of lysostaphin was effective against the highly antibiotic-resistant MRSA strains.

Two advantages of lysostaphin over current antibiotics used for topical therapy are the high potency of lysostaphin and its effectiveness on strains resistant to other antibiotics. Another advantage is that the drug lacks the toxicity inherent in vancomycin use.

EXAMPLE 1

Lysostaphin Treatment of Staphylococcus keratitis

To determine the efficacy of lysostaphin treatment of methicillin-resistant and methicillin-sensitive *Staphylococcus aureus* keratitis, a rabbit model was used. The rabbit model is a standard technique to test new ocular treatments for use in humans, including evaluating effects of new ocular antibiotics. Methicillin-resistant *S. aureus* strain 301 (MRSA 301) or methicillin-sensitive strain ISP546 were intrastromally injected into thirty-six rabbit corneas. The treated corneas were then divided into three groups: 12 corneas to be treated with 5% aqueous vancomycin; 12, to be treated with 0.28% aqueous lysostaphin; and 12, as an untreated control group. Each of the three groups were then divided into an early treatment group ("early therapy") and a late treatment group ("late therapy"). The early therapy group was treated topically every 30 minutes for 5 hr beginning at 4 hr post-infection. The late therapy group was treated topically every 30 minutes for 5 hr beginning at 10 hr post-infection. One hour after the last treatment, the six corneas from each treatment group, including the untreated control group, were removed, homogenized, and cultured to determine the number of colony forming units (CFU) per cornea. The results for the corneas injected with MRSA 301 are shown in Table 1.

TABLE 1

Antibiotic Treatment of Experimental Keratitis (MRSA strain 301)

| Treatment | Early Therapy (Log CFU) | Late Therapy (Log CFU) |
| --- | --- | --- |
| Lysostaphin (0.28%) | 0.00 ± 0.00 | 0.85 ± 0.46 |
| Vancomycin (5%) | 2.30 ± 0.85 | 5.83 ± 0.16 |
| Untreated | 6.52 ± 0.10 | 6.59 ± 0.12 |

With early therapy (beginning at 4 hr post-infection), lysostaphin sterilized all MRSA 301-infected corneas, while untreated corneas contained 6.52 log CFU/cornea ($P \leq 0.0001$). No MRSA 301-infected corneas treated with vancomycin became sterile; these corneas retained 2.3±0.85 log CFU/cornea. When therapy was begun later (10–15 hours post-infection), lysostaphin reduced the CFU/cornea of MRSA 301 to 0.85±0.46 log CFU/cornea, compared to 6.59±0.12 log CFU/cornea of the untreated group ($P \leq 0.0001$). Late vancomycin therapy failed to produce a significant decrease in CFU/cornea relative to the untreated control (5.83±0.16 log CFU/cornea; P=0.1364).

Moreover, with early therapy, lysostaphin reduced the CFU/cornea of the ISP546 strain to 0.58±0.34 log CFU/cornea compared to 5.94±0.24 log CFU/cornea of the untreated group ($P \leq 0.0001$). Vancomycin did not significantly reduce the number of ISP546 CFU/cornea compared to the control group (5.41±0.11; P=0.3677).

Staphylococcus keratitis has been successfully treated with topical drops of lysostaphin. Lysostaphin killed MRSA strains replicating in the cornea significantly better than did vancomycin, and also killed non-replicating Staphylococcus in the cornea better than any of the following sixteen antibiotics tested: tobramycin (0.3 or 1.36%), gentamicin (0.3%), amikacin (0.3%), cephalothin (0.3%), erythromycin (0.3%), minocycline (0.3%), teracycline (0.3%), clarithromycin (0.3%), ciprofloxacin (0.3%), ofloxacin (0.3%), norfloxacin (0.3%), vancoymcin (5%), polymyxin (10,000 Units/ml), trimethoprim (1.0%), daptomycin (0.1%), and mupirocin (0.27%). (data not shown).

No ocular isolate of *S. aureus* tested has shown resistance to lysostaphin, including isolates of MRSA strains known to be resistant to fluoroquinolones. Nearly all strains of S. aureus were susceptible to lysostaphin at concentrations less than 1 μg/ml; the MIC for MRSA strains was 0.04 μg/ml, a value nearly 50-fold lower than the typical MIC for fluoroquinolones (2 μg/ml) applied to MRSA strains known to be susceptible to fluoroquinolones.

Lysostaphin is more effective than any currently available drug for treating Staphylococcus keratitis. When applied as a single topical drop (0.3%) every 30 min from 4 to 9 hr post-infection, or from 10 to 15 hr post-infection, lysostaphin caused significant reductions in the number of Staphylococcus CFU per cornea.

EXAMPLE 2

Penetration of lysostaphin into the cornea

Lysostaphin was shown to penetrate the cornea in the following experiments. Rabbit eyes were infected with *S. aureus* and then treated as described above in Example 1. Treated eyes showed no signs of infection for more than one week. The untreated controls developed distinctive signs of infection by 10 hr and had severe corneal symptoms as determined by the Slit Lamp Examination Score (SLE=19) by 24 hr. A normal eye has a SLE value of 0, while a theoretical maximally inflamed eye would have a SLE of 28.

In a second experiment, the effect of lysostaphin during post-treatment processing of the corneas was inhibited. Rabbit eyes infected with *S. aureus* were treated with lysostaphin as described in Example 1, except that during the processing of the corneas all lysostaphin activity was inhibited by adding zinc ions. Corneas were washed in situ with 50 mM Tris HCl buffer, pH 7.5, with 150 mM NaCl and 200 mM ZnCl. Immediately on harvesting, the corneas were placed into the same buffer. Zinc ion is a known inhibitor of lysostaphin, preventing its anti-bacterial action. Thus little bacterial killing due to lysostaphin could occur during the harvesting and processing of the corneas. The lysostaphin-treated corneas were again free of viable bacteria while untreated corneas, also washed in situ and placed in a zinc solution, contained over 6 logs of CFU per cornea.

Without wishing to be bound by this theory, it is believed that despite its size lysostaphin penetrated the cornea aided by its proteolytic activity as a zinc metalloproteinase, as described by Park et al., "Binding and Degradation of Elastin by the Staphylolytic Enzyme Lysostaphin," Int. J. Biochem. Cell Biol., vol. 27, pp. 139–146 (1995).

EXAMPLE 3

No inflammatory or toxic reaction to lysostaphin

An important question for any new drug treatment is whether the drug will elicit an inflammatory response. The topical application of lysostaphin caused no inflammatory or toxic reactions in the rabbit eye. For rabbit eyes infected and treated as in Example 1, there were no differences in the SLE scores of the lysostaphin-treated eyes versus untreated and uninfected eyes ("normal" eyes). The SLE scores of lysostaphin-treated eyes were identical to those treated with an equal number of applications of water or buffered saline. In contrast, eyes treated with vancomycin showed a significant increase in SLE score relative to untreated eyes (P=0.0163, data not shown).

EXAMPLE 4

Interaction of lysostaphin with other antibiotics

Lysostaphin is an extremely potent killer of *S. aureus*, but lacks activity on Gram-negative bacteria and other microbial agents (e.g., acid-fast bacteria). Lysostaphin therapy has a potential to be used in conjunction with other antibiotic therapy. Lysostaphin will be tested in conjunction with other antibiotics, including cephalothin, vancomycin, ciprofloxacin, ofloxacin, erythromycin, gentamicin, and tobramycin. The effectiveness of each of these antibiotics alone has been tested in the rabbit model of keratitis. Multiple bacterial strains will be tested in the cornea, for example, *Staphylococcus aureus*, Serratia, and Pseudomonas. The infections will be treated with lysostaphin plus another antibiotic. A test antibiotic will be administered every 30 min from 4 to 9 hr post-infection. Five minutes after each application of test antibiotic, a topical drop of lysostaphin (0.3%) will be administered. In these experiments, there will be an untreated group and a group treated with the test antibiotic alone, and a group treated with lysostaphin alone (4 corneas per group). All eyes will undergo SLE scoring at 4 and 10 hr post-infection for Staphylococcus, and at 16 and 27 hr for Psuedomonas and Serratia. One hour after the last drug application (10 hr post-infection for Staphylococcus and 27 hr post-infection for Pseudomonas and Serratia), the corneas will be harvested and the CFU per cornea determined. The SLE scores and CFU per cornea for the groups treated with a single antibiotic versus those treated with the antibiotic combination will be compared. It is expected that lysostaphin will demonstrate no inhibitory interactions with other drugs and that lysostaphin may be combined with other antibiotics for treatment of a broader range of bacteria.

EXAMPLE 5

Uptake and retention of lysostaphin in the cornea and aqueous humor

The changes in lysostaphin concentration in the cornea and aqueous humor will be measured during and after therapy to determine the pharmacokinetics. Normal corneas and corneas infected with Staphylococcus for 4 hr will be topically treated with 0.3% lysostaphin every 30 min for 5 hr. Corneas (six per group) will be assayed for lysostaphin 30 min after the first application, one hour after the first application, and every hour thereafter for a total of 8 hr. The assay of lysostaphin will be performed by four methods: bacterial lysis, bacterial killing, enzyme activity, and ELISA assay. Bacterial lysis assays are spectrophotometric determinations of bacterial lysis using a suspension of *S. aureus* in buffer (a reduction in optical density at 600 nm) according to the procedure of Kline et al., "A colorimetric microtiter plate assay for lysostaphin using a hexaglycine substrate," Analytical Biochemistry, vol. 217, pp. 329–331 (1994). Bacterial killing assays will determine the reduction in CFU/ml caused by the incubation of Staphylococcus for 1 hr with samples containing lysostaphin. The enzyme assay and the ELISA assay will be conducted by the procedure of E. Harlow et al., "Antibodies: A laboratory manual," Cold Spring Harbor Laboratory, New York (1988).

It is expected that lysostaphin will penetrate the cornea and accumulate in the aqueous humor at low concentrations. The extensive bacteria killing is probably due to lysostaphin's effectiveness at much lower levels than required for other antibiotics.

EXAMPLE 6

Dose effects of lysostaphin

When comparing antibiotics in the rabbit keratitis model, a standard 0.3% solution of lysostaphin has been applied every 30 min for 5 hr as described in Example 1. To determine the effect of other concentrations, lysostaphin will be formulated to its maximal practical concentration (potentially 5%) and then diluted serially to test both the antibiotic effect and any adverse ocular effects. The effectiveness and irritating aspects of four concentrations above 0.3% and four concentrations below 0.3% will be tested. A topical application of lysostaphin will be applied every 30 min from 4 to 9 hr post-infection. Effectiveness will be measured by reductions in CFU per cornea relative to untreated corneas at 10 hr post-infection. The adverse effects will be measured by SLE scoring at 4, 7, and 10 hr post-infection and by determinations of myeloperoxidase activity ("MPO") at 10 hr post-infection.

It is expected that concentrations up to 5% lysostaphin can be obtained and that a repeated topical application of 5% lysostaphin could achieve an intra-corneal concentration of 5 µg/ml.

EXAMPLE 7

Immune complications of lysostaphin therapy

Because lysostaphin is a protein, the possibility of an immune response to the molecule must be considered. Two aspects of an immune response will be considered: first, production of antibodies could neutralize the bactericidal activity of lysostaphin; and second, an immune response can result in inflammation or tissue damage (an allergic reaction). Normal (uninfected) rabbits will be topically treated with lysostaphin every 30 min for 5 hr. This will be repeated every two weeks for a total of five treatments. Immediately prior to treatment, the rabbits will undergo SLE scoring and will be bled to obtain sera. On each treatment day, the eyes will be evaluated by SLE scoring immediately after the last application of the drug, then 12, 24, and 48 hr later.

The SLE scoring will determine if any inflammatory or damaging immune reactions appear as a result of repeated lysostaphin application. The sera obtained during weeks 2, 4, 6, and 8 will be used to determine if antibodies are produced. The serum from the first bleeding (immediately before treatment) will serve as the negative control. Antibody will be detected and quantified by an antibody capture ELISA assay. The ability of any antiserum to block lysostaphin activity will be tested in a bacterial lysis assay.

It is expected that any antibody production to lysostaphin applications will be low and will not interfere with lysostaphin activity. It is also expected that lysostaphin will not cause any adverse effects. If antibodies are formed and inhibit drug action or induce allergic reactions, then patients could be treated for a short duration and for only one episode. Given the value of this drug for highly resistant forms of Staphylococcus, this limited use would still be valuable for these patients.

The term "therapeutically effective amount" as used herein for treatment of keratitis refers to an amount of lysostaphin sufficient to decrease a subject's ocular Staphylococcus infection to a statistically significant degree or to decrease the symptoms of a Staphylococcus infection to a statistically significant degree. Ordinary persons skilled in the art would recognize that the effect of lysostaphin on a human eye infected with Staphylococcus would correlate with the effects seen in the rabbit eye, a common model used to evaluate new ocular antibiotics.

Pharmaceutically acceptable carrier preparations for topical administration of lysostaphin include sterile, aqueous or non-aqueous solutions, suspensions, and emulsions. Examples of non-aqueous solvents are propylene glycol, polyethylene glycol, vegetable oils, and organic esters such as ethyl oleate. Aqueous carriers include water, alcoholic/aqueous solutions, emulsions or suspensions, including saline and buffered media. This would include sodium chloride solution, Ringer's, ionic resins, or fixed oils. The active lysostaphin may be mixed with excipients that are pharmaceutically acceptable and are compatible with the lysostaphin. Suitable excipients include water, saline, dextrose, glycerol and ethanol, or combinations thereof. The lysostaphin may also be mixed with pharmaceutically acceptable carriers to form an ointment, including hydrophilic petrolatum, petrolatum, white petrolatum, mineral oils, or lanolin.

Lysostaphin may also be mixed with other drugs, including antiinflammatory steroids and antibiotics to treat a broader range of bacteria causing ocular infections.

The complete disclosures of all references cited in this specification are hereby incorporated by reference. Also incorporated by reference is the complete disclosure of an Abstract by J. J. Dajcs et al., "Lysostaphin is effective in treating methicillin-resistant and methicillin-sensitive *Staphylococcus aureus* keratitis," IOVS, vol. 40, p. S262 (1999), to be presented at the 1999 meeting for the Association for Research in Vision and Ophthalmology, Fort Lauderdale, Fla., May 10, 1999. In the event of an otherwise irreconcilable conflict, however, the present specification shall control.

I claim:

1. A method to treat Staphylococcus ocular keratitis in the stromal layer of the cornea in a mammal, comprising the topical application of a therapeutically effective amount of lysostaphin to the cornea, wherein the lysostaphin penetrates through the outer epithelial layer of the cornea to reach the stromal layer.

2. The method of claim 1, wherein the ocular keratitis is due to *Staphylococcus aureus*.

3. The method of claim 1, wherein the ocular keratitis is due to *Staphylococcus epidermidis*.

4. The method of claim 1, wherein the lysostaphin is applied in a concentration between about 0.1% w/v and about 5% w/v.

5. The method of claim 1, wherein the lysostaphin is applied in a concentration about 0.3% w/v.

6. The method of claim 1, wherein the lysostaphin is applied in combination with a pharmaceutically acceptable carrier.

7. The method of claim 1, wherein the lysostaphin is applied in combination with another ocular medication.

8. A method to treat Staphylococcus ocular keratitis in the stromal layer of the cornea in a human, comprising the topical application of a therapeutically effective amount of lysostaphin to the cornea, wherein the lysostaphin penetrates through the outer epithelial layer of the cornea to reach the stromal layer.

9. The method of claim 8, wherein the ocular keratitis is due to *Staphylococcus aureus*.

10. Th method of claim 8, wherein the ocular keratitis is due to *Staphylococcus epidermidis*.

11. The method of claim 8, wherein the lysostaphin is applied in a concentration between about 0.1% w/v and about 5% w/v.

12. The method of claim 8, wherein the lysostaphin is applied in a concentration about 0.3% w/v.

13. The method of claim 8, wherein the lysostaphin is applied in combination with a pharmaceutically acceptable carrier.

14. The method of claim 8, wherein the lysostaphin is applied in combination with another ocular medication.

* * * * *